(12) United States Patent
Beisswenger et al.

(10) Patent No.: US 6,498,193 B2
(45) Date of Patent: Dec. 24, 2002

(54) TREATMENT FOR COMPLICATIONS OF TYPE 2 DIABETES

(75) Inventors: Paul J. Beisswenger, Hanover, NH (US); Benjamin S. Szwergold, Hanover, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 09/735,683

(22) Filed: Dec. 13, 2000

(65) Prior Publication Data

US 2001/0031790 A1 Oct. 18, 2001

Related U.S. Application Data

(60) Provisional application No. 60/171,378, filed on Dec. 22, 1999.

(51) Int. Cl.⁷ ............................................. A61K 31/155
(52) U.S. Cl. ..................................................... 514/635
(58) Field of Search .......................................... 514/635

(56) References Cited

U.S. PATENT DOCUMENTS 3,174,901 A    3/1965   Stern et al. ................... 167/65

OTHER PUBLICATIONS

Beisswenger et al., Diabetes, 48/1, pp. 198–202 (Jan., 1999) (abstract).*

Ruggiero–Lopez et al., Biochemical Pharmacology, 58/11, pp. 1765–1773 (Dec. 1, 1999)(abstract).*

Jyothirmayi et al., J. Cardiovascular Pharmacology and Therapeutics, 3(4), 319–326 (1998).*

Ruggiero et al., Diabetologia 40, suppl. 1, A310 (1997)(abstract).*

Tanaka et al., Current Therap. Res., 58(10), 693–697 (Oct. 1, 1997).*

* cited by examiner

*Primary Examiner*—Phyllis G. Spivack
(74) *Attorney, Agent, or Firm*—Licata & Tyrrell P.C.

(57) ABSTRACT

A method is disclosed of lowering plasma levels of α-dicarbonyl precursors of advanced glycation end-products, such as methylglyoxal, in a patient having type 2 diabetes by administrating metformin in a dosage from twenty-five to fifty percent in excess of its antidiabetic therapeutic regimen. The high dosage of metformin acts to reduce plasma levels of α-dicarbonyl compounds by a mechanism distinct from that whereby it exerts its antidiabetic activity.

5 Claims, No Drawings

TREATMENT FOR COMPLICATIONS OF TYPE 2 DIABETES

This invention relates to the use of metformin in increased dosages to treat or prevent long-term complications that often characterize type 2 diabetes. This application claims benefit of priority of U.S. Provisional Patent Application No. 60/171,378 filed Dec. 22, 1999.

BACKGROUND OF THE INVENTION

Metformin, i.e. N,N-dimethylimidocarbonimide diamide, is a known compound approved by the U.S. Food & Drug Administration for the therapeutic treatment of diabetes. The compound and its preparation are disclosed, for example, in U.S. Pat. No. 3,174,901, issued May 23, 1965. It is known that metformin is effective in the treatment of type 2 diabetes, otherwise known as non-insulin-dependent diabetes mellitus (NIDDM). Metformin was the first oral antidiabetic agent introduced that is chemically and pharmacologically unrelated to the oral sulfonylurea diabetic agents, such as tolbutamide.

A statement used to describe metformin in the Informed Drug Guide is that proof that it has an advantageous effect on the prognosis of diabetes (complications, mortality) does not exist. In accordance with the present invention, it has unexpectedly been found that metformin does exert an effect against long term complications that are frequently associated with type 2 diabetes. This effect, not previously known, is quite possibly due to a mechanism of activity separate and distinct from its hypoglycemic activity.

SUMMARY OF THE INVENTION

The invention relates to the use of metformin in a dosage regimen significantly higher than its established therapeutic antidiabetic dosage as a treatment/preventative against long-term complications of type 2 diabetes as might normally occur during extended therapy of the disease. This activity would typically not manifest itself during the administration of metformin in the generally prescribed therapeutic dosage ranges.

DETAILED DESCRIPTION OF THE INVENTION

Recent studies devoted to the common long term complications of type 2 diabetes have shown that chronic hyperglycemia and its resultant glucose toxicity play an important role in the development of complications such as retinal and renal disease. It has further been found that glucose toxicity is mediated through increased production by the body of highly chemically reactive α-dicarbonyl precursors of advanced alycation end products (AGEs). Such toxins, particularly methylglyoxal (MG) have been shown to be extremely reactive as glycating agents for collagen, enzymes, and other important cellular components. MG has been shown to be toxic to cultured cells.

It has been demonstrated that MG is present in elevated levels in individuals manifesting evidence of early diabetic nephropathy and retinopathy. MG has the capacity to stimulate the formation of advanced glyceration end products, which are in turn associated with diabetic vascular complications. Hence, those of ordinary skill in the art will appreciate that a treatment having the effect of materially reducing the level of such α-dicarbonyl compounds will have a significant effect in the prevention of long-term diabetic vascular complications.

There exist both oxidative and reductive pathways for the breakdown of MG. Once the mechanisms involving α-dicarbonyls and their influence, directly or indirectly, on long-term complications of diabetes began to come to light, efforts were undertaken to discover agents that might have the unique capacity to inactivate or block them. It has been found that inactivation of α-dicarbonyl toxins, such as MG, produces a preventative or therapeutic effect against such conditions. Such a treatment is provided in accordance with the present invention. The use of metformin to accomplish this result is particularly significant since it is already established as a therapy of choice for type 2 diabetes.

In accordance with the present invention, it has been found that metformin possesses significant activity in protecting against the production of MG, or decreased detoxification associated with increasing degrees of hyperglycemia. Unexpectedly, it has been found that this capacity of metformin appears to be unrelated to differences in glycemic control, thus suggesting that the ability of metformin to protect against long-term complications of type 2 diabetes is mechanistically independent of its antihyperglycemic effect. This effect was observed in a study of groups of patients receiving high and low dosages, respectively, of metformin in comparison to healthy control group and a diabetic control group not receiving metformin. It was found that there was little difference in glycemic control between the group taking high and low dosages, respectively, of metformin. However, in the group taking high dosages of metformin, It was observed that the drug produced a significant lowering of plasma levels of MG.

Those of ordinary skill in the medical and pharmaceutical arts are well aware of the fact that, regardless of the demonstrated safety of a medicinal molecule within its recommended clinical dosage range, the physician's objective in prescribing is to achieve the maximum desired therapeutic effect with the minimum effective dosage for a given patient. By utilizing the minimum effective dosage, the desired therapeutic effect can be realized with a minimum of untoward side-effects, potential for drug interaction and the like. For this reason, the argument that the therapeutic method of the present invention is inherent in the present therapeutic use of metformin does not appear well founded since the present method requires that an excess of metformin be given over that required for its antidiabetic effect.

The method of the present invention can be termed a therapeutic method in the context that it produces a significant lowering of the plasma levels of methylglyoxal, a known toxin. It may also be termed a preventative or prophylactic method in the context that elevated levels of methylglyoxal has been demonstrated in patients showing evidence of diabetic nephropathy and retinopathy. Regardless, it appears that this mechanism of action of metformin is mechanistically distinct from its recognized antidiabetic effect.

Without wishing to be bound by any theory, it is believed that metformin in high dosages asserts its activity in accordance with the method of the invention by a binding effect of the guanidino group of metformin with the α-dicarbonyl group of MG. This binding effect in vivo results in a reduction in MG levels and, thereby, potentially inhibits tissue glycation. Another possible explanation is that metformin enhances the high-capacity glyoxalase pathway by which MG is broken down. However, while levels of the metabolite of this mechanism, D-lactate, are increased by the administration of metformin, there is no significant difference in the amount thereof in high dosages vs. low dosages in comparison to the diabetic control group receiving no metformin. Hence, it is believed that the binding effect with MG is the more likely explanation.

The differences noted above are shown in the following summary of clinical results utilizing patient groups of individuals free of diabetes, those having diabetes but receiving no metformin, those having diabetes and receiving one gram or less of metformin daily and those receiving more than a gram of metformin daily, respectively. In Table 1, the number of patients in each group is noted as are the levels of plasma MG, DL(D-lactate) and plasma glucose ($HbA_{1c}$).

TABLE 1

| Treatment Group | n | MG (nmol/l) | DL μmol/l | $HbA_{1c}$ (%) |
|---|---|---|---|---|
| Control Subjects | 28 | 123.0 ± 37.0 | 8.3 ± 3.1 | 5.2 ± 0.5 |
| Diabetic Subjects | | | | |
| No Metformin | 27 | 189.3 ± 38.7[a] | 10.4 ± 3.9 | 8.2 ± 1.2 |
| Metformin | | | | |
| ≦1 g/day | 17 | 210.9 ± 51.0 | 13.8 ± 7.7[c] | 8.0 ± 1.1 |
| >1 g/day | 13 | 158.4 ± 44.2[b] | 13.4 ± 4.6[c] | 8.3 ± 1.0 |

[a]indicates a statistically significant difference as compared to control subjects
[b]indicates a statistically significant difference as compared to no metformin diabetics and low dose metformin subjects
[c]indicates a statistically significant difference as compared to no metformin diabetics As is evident from the data in Table 1, the group receiving a higher dosage of metformin had a significantly lower plasma level of MG than the group whose metformin dosage was less than one gram per day. Further, we have found that, in the absence of such increased levels of metformin, there is a strong association between glycemic control, based on $HbA_{1c}$ or fasting plasma glucose levels, and MG levels in a population composed of type 2 diabetic subjects who are not receiving metformin. This increase in MG levels is not seen in patients receiving high levels of metformin in accordance with the method of the present invention, a result that indicates metformin protects against MG production or decreased detoxification that is associated with increasing degrees of hyperglycemia.

In accordance with the subject method, metformin is administered to patients being treated for type 2 diabetes in a dosage sufficiently in excess of the usual antidiabetic therapeutic dosage so that a marked reduction in the plasma level of MG is achieved. It is realized that metformin is commercially available is tablets containing 500 mg, 850 mg and 1000 mg and that the initial dosage for a given patient to achieve anti diabetic goal typically is 1000 mg per day. Later in the course of treatment the total may be as much as 2000 or 2500 mg in divided doses. It must be borne in mind that, in the typical clinical situation, the initial dosage established for metformin in type 2 diabetes would be the effective anti-diabetic dosage. It is that effective anti-diabetic dosage which is increased in order to realize the therapeutic effect provided by the method of the present invention.

Those of ordinary skill in the art will be aware of the fact that a given dosage of metformin may be a therapeutically effective dosage for one individual and represent a material excess for another. Hence, although the present method generally contemplates administration of a daily dosage of metformin of up to and including one gram as representative antidiabetic or antihyperglycemic therapeutic dosage and a dosage in excess of one gram as representing an effective dosage for the present method, the relative amounts are best expressed in a percentage ratio. In general we have found that an amount of metformin exceeding the anti-diabetic therapeutic dosage by at least twenty five percent, preferably at least fifty percent is effective in producing a material reduction in the plasma level of MG. It is appreciated that these amounts may have to be adjusted in view of the dosage forms presently available.

It is further readily appreciated by those of ordinary skill in the art that there is a maximum dosage of metformin that can be safely administered and that the method of the invention is intended to have as its upper percentage a dosage well within that maximum. While an approximately fifty percent excess is a preferred dosage of metformin for the present method, it is anticipated that the clinician will adjust the dosage depending on periodic determinations of the level of MG in the blood of the patient, and may lower it to a dosage close to or the same as the antihyperglycemic therapeutic level once it is determined that the plasma levels of MG has been reduced to a safe level. The method of the present invention is uniquely advantageous in that the dosage of metformin required to reduce the plasma level of MG encompasses the typical therapeutic range.

The method of the present invention is intended to be carried out primarily when a patient undergoing therapy with metformin is diagnosed as having an elevated plasma level of MG or of plasma or tissue proteins modified by MG. At such time, the dosage of metformin would be increased in accordance with the method of the invention to thereby reduce the level of MG back to a tolerable range. Alternatively, when factors such as the age and clinical profile of the patient indicate a propensity to high plasma levels of MG, the increased dosage of metformin according to the method of the invention would be administered routinely as a prophylaxis against the development of complications.

The method of the present invention is applicable to the administration of metformin by known routes of administration. However, as metformin is available commercially in the form of tablets, they would be the preferred mode of administration. Pharmaceutical tables containing metformin are prepared in accordance with accepted practices in the art utilizing inert pharmaceutical excipient materials approved for such use. Such tablets may contain any convenient dosage and may be single or double scored for ease of dosage adjustment by the patient in a given clinical situation.

What is claimed is:

1. A method of treating a patient having type 2 diabetes to prevent long term complications of the disease associated with elevated plasma levels of reactive α-dicarbonyl precursors of advanced glycation end products comprising administering to said patient an amount of metformin from twenty-five to fifty percent in excess of the therapeutic anti-diabetic dosage for said patient thereby reducing the plasma levels of said precursors.

2. The method of claim 1, wherein the metformin is administered in at least twenty five percent excess of the therapeutic antidiabetic dosage.

3. The method of claim 1, wherein the metformin is administered in at least fifty percent excess of the therapeutic antidiabetic dosage.

4. The method of claim 1, wherein said reactive α-dicarbonyl precursor is methylglyoxal.

5. The method of claim 1, wherein the patient manifests evidence of early diabetic nephropathy, retinopathy or atherosclerosis.

* * * * *